US012653943B2

(12) United States Patent
     Locke

(10) Patent No.: US 12,653,943 B2
(45) Date of Patent: Jun. 16, 2026

(54) SYSTEMS, METHODS, AND APPARATUSES TO OVERCOME PUMP-INDUCED PRESSURE EXCURSIONS AND CONTROL ALIASING WITH REDUCED VOLUME, ABSORBENT NEGATIVE-PRESSURE THERAPY SYSTEMS

(71) Applicant: KCI Manufacturing Unlimited Company, Westmeath (IE)

(72) Inventor: Christopher Brian Locke, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 104 days.

(21) Appl. No.: 18/039,281

(22) PCT Filed: Nov. 11, 2021

(86) PCT No.: PCT/IB2021/060453
     § 371 (c)(1),
     (2) Date: May 29, 2023

(87) PCT Pub. No.: WO2022/123352
     PCT Pub. Date: Jun. 16, 2022

(65) Prior Publication Data
     US 2024/0009375 A1     Jan. 11, 2024

Related U.S. Application Data

(60) Provisional application No. 63/122,310, filed on Dec. 7, 2020.

(51) Int. Cl.
     *A61M 1/00*      (2006.01)
     *F15B 1/04*      (2006.01)

(52) U.S. Cl.
     CPC ................ *A61M 1/96* (2021.05); *A61M 1/78* (2021.05); *F15B 1/04* (2013.01); *F15B 2201/22* (2013.01)

(58) Field of Classification Search
     CPC ...... F15B 2201/22; F15B 2201/00–615; F15B 1/24; A61M 1/7411–743
     See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| (Continued) | | |

FOREIGN PATENT DOCUMENTS

| | | |
|---|---|---|
| AU | 550575 B2 | 3/1986 |
| AU | 745271 B2 | 3/2002 |
| (Continued) | | |

OTHER PUBLICATIONS

International Search Report and Written Opinion for PCT International Application No. PCT/IB2021/060453, mailed Apr. 4, 2022.

(Continued)

*Primary Examiner* — Leslie R Deak
*Assistant Examiner* — Linnae E. Raymond

(57) ABSTRACT

A pneumatic accumulator may be fluidly coupled between a negative-pressure source and a dressing of a therapy system. The pneumatic accumulator may have a small volume and one or more deformable members that can deform under negative pressure, reducing the volume of the pneumatic accumulator. The pneumatic accumulator can smooth a pressure wave created by the negative-pressure source. The pneumatic accumulator may also provide additional negative-pressure storage capacity to the therapy system. For example, if a leak develops at the dressing, some of the negative pressure stored in the pneumatic actuator may be (Continued)

supplied to the dressing. The pneumatic accumulator may allow for reduced runtime of the negative-pressure source, leading to increased electrical efficiency.

14 Claims, 7 Drawing Sheets

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,896,787 A * | 7/1959 | Roman | A01J 11/06 |
| | | | 210/406 |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,191,204 A * | 3/1980 | Nehring | A61M 1/743 |
| | | | 128/205.12 |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,476,448 A * | 12/1995 | Urich | A61M 1/74 |
| | | | 138/30 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 10,583,228 B2 * | 3/2020 | Shuler | A61M 1/77 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0274229 A1 * | 10/2010 | Duocastella Codina | |
| | | | A61M 1/684 |
| | | | 604/317 |
| 2013/0144227 A1 * | 6/2013 | Locke | A61M 1/743 |
| | | | 604/319 |
| 2014/0074053 A1 * | 3/2014 | Locke | A61F 13/05 |
| | | | 156/60 |
| 2014/0163491 A1 | 6/2014 | Schuessler et al. | |
| 2014/0243766 A1 | 8/2014 | Martuch | |
| 2015/0080788 A1 | 3/2015 | Blott et al. | |

(56) References Cited

U.S. PATENT DOCUMENTS

| | | | | |
|---|---|---|---|---|
| 2015/0141907 | A1* | 5/2015 | Clement | A61B 18/1482 604/28 |
| 2019/0290813 | A1 | 9/2019 | Luckemeyer et al. | |

FOREIGN PATENT DOCUMENTS

| | | | | |
|---|---|---|---|---|
| AU | 755496 | B2 | 12/2002 | |
| CA | 2005436 | A1 | 6/1990 | |
| DE | 2640413 | A1 | 3/1978 | |
| DE | 4306478 | A1 | 9/1994 | |
| DE | 29504378 | U1 | 9/1995 | |
| DE | 19511469 | C1* | 10/1996 | A61M 39/10 |
| DE | 102006054628 | A1* | 3/2008 | A61M 1/77 |
| EP | 0100148 | A1 | 2/1984 | |
| EP | 0117632 | A2 | 9/1984 | |
| EP | 161865 | A2 | 11/1985 | |
| EP | 358302 | A2 | 3/1990 | |
| EP | 1018967 | A1 | 7/2000 | |
| EP | 3202430 | A1* | 8/2017 | A61M 1/0003 |
| GB | 692578 | A | 6/1953 | |
| GB | 2195255 | A | 4/1988 | |
| GB | 2197789 | A | 6/1988 | |
| GB | 2220357 | A | 1/1990 | |
| GB | 2235877 | A | 3/1991 | |
| GB | 2329127 | A | 3/1999 | |
| GB | 2333965 | A | 8/1999 | |
| JP | H0589901 | U* | 12/1993 | F15B 1/103 |
| JP | 4129536 | B2 | 8/2008 | |
| SG | 71559 | | 4/2002 | |
| WO | 80/02182 | A1 | 10/1980 | |
| WO | 8704626 | A1 | 8/1987 | |
| WO | 90010424 | A1 | 9/1990 | |
| WO | 93009727 | A1 | 5/1993 | |
| WO | 94020041 | A1 | 9/1994 | |
| WO | 9605873 | A1 | 2/1996 | |
| WO | 97/18007 | A1 | 5/1997 | |
| WO | 99/13793 | A1 | 3/1999 | |
| WO | 2013078214 | A1 | 5/2013 | |
| WO | 2013123022 | A1 | 8/2013 | |
| WO | 2023012551 | A1 | 2/2023 | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. YU.N., et al; "Active Wound Drainage", Vestnki Khirurgi, vol. 138, Issue 4, 1987, and 7 page English translation thereof.

Davydov, YU.A., et al; "Bacteriological and Cytological Assessment of Vacuum Therapy for Purulent Wounds"; Vestnik Khirugi, Oct. 1988, pp. 48-52, and 8 page English translation thereof.

Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and

(56)                References Cited

OTHER PUBLICATIONS

Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1968) ("Solovev Abstract").

V.A.C. ® Therapy Clinical Guidelines: A Reference Source for Clinicians; Jul. 2007.

European Examination Report for corresponding Application No. 232179010, dated Feb. 12, 2026.

\* cited by examiner

1

SYSTEMS, METHODS, AND APPARATUSES TO OVERCOME PUMP-INDUCED PRESSURE EXCURSIONS AND CONTROL ALIASING WITH REDUCED VOLUME, ABSORBENT NEGATIVE-PRESSURE THERAPY SYSTEMS

CROSS-REFERENCE TO RELATED APPLICATIONS

This application claims the benefit of priority to U.S. Provisional Application No. 63/122,310, filed on Dec. 7, 2020, which is incorporated herein by reference in its entirety.

TECHNICAL FIELD

The invention set forth in the appended claims relates generally to tissue treatment systems and more particularly, but without limitation, to fluid conductors for fluidly coupling a negative-pressure source to a dressing.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for a pneumatic accumulator in a negative-pressure therapy environment are set forth in the appended claims. Illustrative embodiments are also provided to enable a person skilled in the art to make and use the claimed subject matter.

For example, in some embodiments, a pneumatic accumulator may be fluidly coupled between a negative-pressure source and a dressing of a therapy system. The pneumatic accumulator may have a small volume and one or more deformable members that can deform under negative pressure, reducing the volume of the pneumatic accumulator. The pneumatic accumulator can smooth a pressure wave created by the negative-pressure source. The pneumatic accumulator may also provide additional negative-pressure storage capacity to the therapy system. For example, if a leak develops at the dressing, some of the negative pressure stored in the pneumatic actuator may be supplied to the dressing. The pneumatic accumulator may allow for reduced runtime of the negative-pressure source, leading to increased electrical efficiency.

Further, in some embodiments an apparatus for reducing pressure spikes at a dressing of a negative-pressure therapy system may include a tubular member, a first end cap, and a second end cap. The tubular member may have a first open end and a second open end. The first end cap may be coupled to the first open end and may include a first wall and a first port. At least a portion of the first wall may be elastomeric. The second end cap may be coupled to the second open end and may include a second wall and a second port. At least a portion of the second wall may be elastomeric. The tubular member, the first end cap, and the second end cap may cooperate to form a chamber having a first volume when the chamber is at ambient pressure. The first port may be fluidly coupled to a negative-pressure port and the second port may be fluidly coupled to the dressing. In response to the application of a negative pressure to the chamber, one or more of the first wall and the second wall may deflect toward one another to reduce the volume of the chamber from the first volume to a second volume.

In other example embodiments, a system for treating a tissue site with negative pressure may include a dressing, a negative-pressure source configured to be fluidly coupled to the dressing, and a pneumatic accumulator configured to be between the dressing and the negative-pressure source. The pneumatic accumulator may include a housing and a deformable portion. The deformable portion may deform under an application of negative pressure. The housing and the deformable portion may define a chamber having a volume in a range of about 2 to about 5 cubic centimeters. The chamber may be fluidly coupled to the dressing and the negative-pressure source.

In yet other example embodiments, an apparatus may include a chamber and a port. The chamber may be fluidly coupled to a negative-pressure source through the port. The chamber may be formed by a rigid wall and an elastomeric wall. The chamber may have an internal volume that is configured to vary between a first volume under ambient pressure and a second volume under negative pressure. The first volume may be in a range of about 2 to about 5 cubic centimeters.

In yet other example embodiments, an apparatus may include a chamber, an inlet port fluidly coupled to the chamber, and an outlet port fluidly coupled to the chamber. The chamber may be formed by a rigid portion and an elastomeric portion. The chamber may have an internal volume that is configured to vary between a first volume under ambient pressure and a second volume under negative pressure. The second volume may be less than the first volume. The first volume may be in a range of about 2 to about 5 cubic centimeters.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
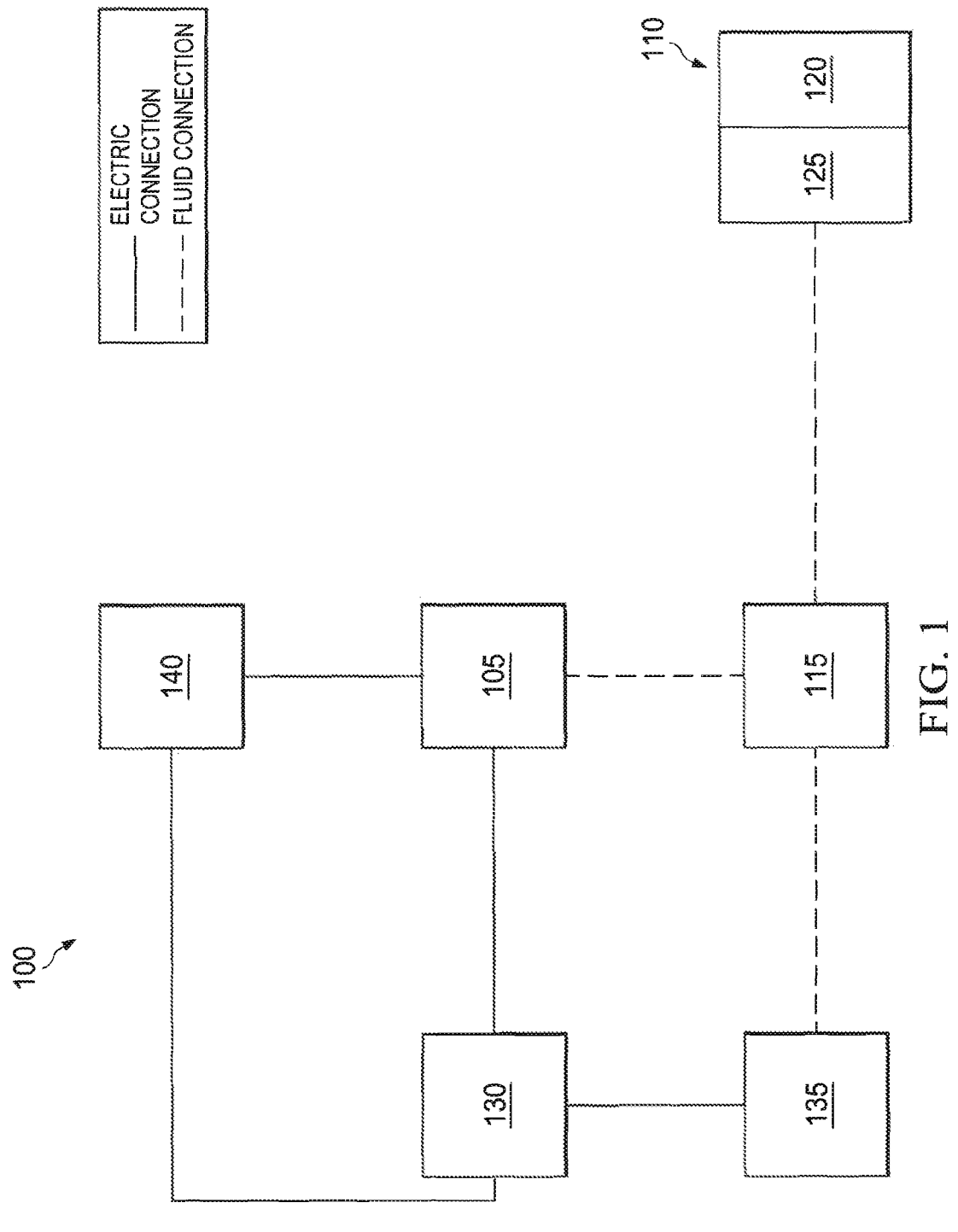
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a pouch 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130 and other components into a therapy unit.

In general, components of the therapy system 100 may be coupled directly or indirectly. For example, the negative-pressure source 105 may be directly coupled to the pouch 115 and may be indirectly coupled to the dressing 110 through the pouch 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The pouch 115 is representative of a container, canister, or other storage component, which can be used to manage exudates and other fluids withdrawn from a tissue site. In some embodiments, the therapy system 100 may not include the pouch 115 and instead exudates and other fluids withdrawn from the tissue site may be stored in the dressing 110, such as for example, within the tissue interface 120.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the tissue interface 120 may include or be formed of an absorbent material. For example, the absorbent material may be a hydrophilic material adapted to absorb fluid from, for example, the tissue site. Suitable absorbent materials may include, without limitation, Luquafleece™ material, Texsus FP2326, BASF 402C, Technical Absorbents 2317 available from Technical Absorbents (www.techabsorbents.com), sodium polyacrylate super absorbers, cellulosics (carboxymethyl cellulose and salts such as sodium CMC), or alginates. In some embodiments, the tissue interface 120 may include one or more layers of absorbent material. In some embodiments, the tissue interface 120 may include one or more layers of wicking material proximate the one or more layers of absorbent material. For example, the tissue interface 120 may include two wicking layers that may surround or otherwise encapsulate the one or more absorbent layers. Suitable wicking materials may include, without limitation, any material having a grain structure capable of wicking fluid, such as, for example, Libeltex™ TDL2 80 gsm. In some embodiments, the dressing 110 may be adapted to provide reduced pressure from the negative-pressure source 105 to the tissue interface 120, and to store fluid extracted from the tissue site in the tissue interface 120.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise Inspire 2301 having an MVTR (upright cup technique) of 2600 g/m²/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in the pouch 115 or the dressing 110.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. For example, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, some therapy systems may increase negative pressure at a rate of about 20-30 mmHg/second, and other therapy systems may increase negative pressure at a rate of about 5-10 mmHg/second. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise rate of negative pressure set at a rate of 25 mmHg/min. and a descent rate set at 25 mmHg/min. In other embodiments of the therapy system 100, the triangular waveform may vary between negative pressure of 25 and 135 mmHg with a rise rate of about 30 mmHg/min. and a descent rate set at about 30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figures 2, 3:
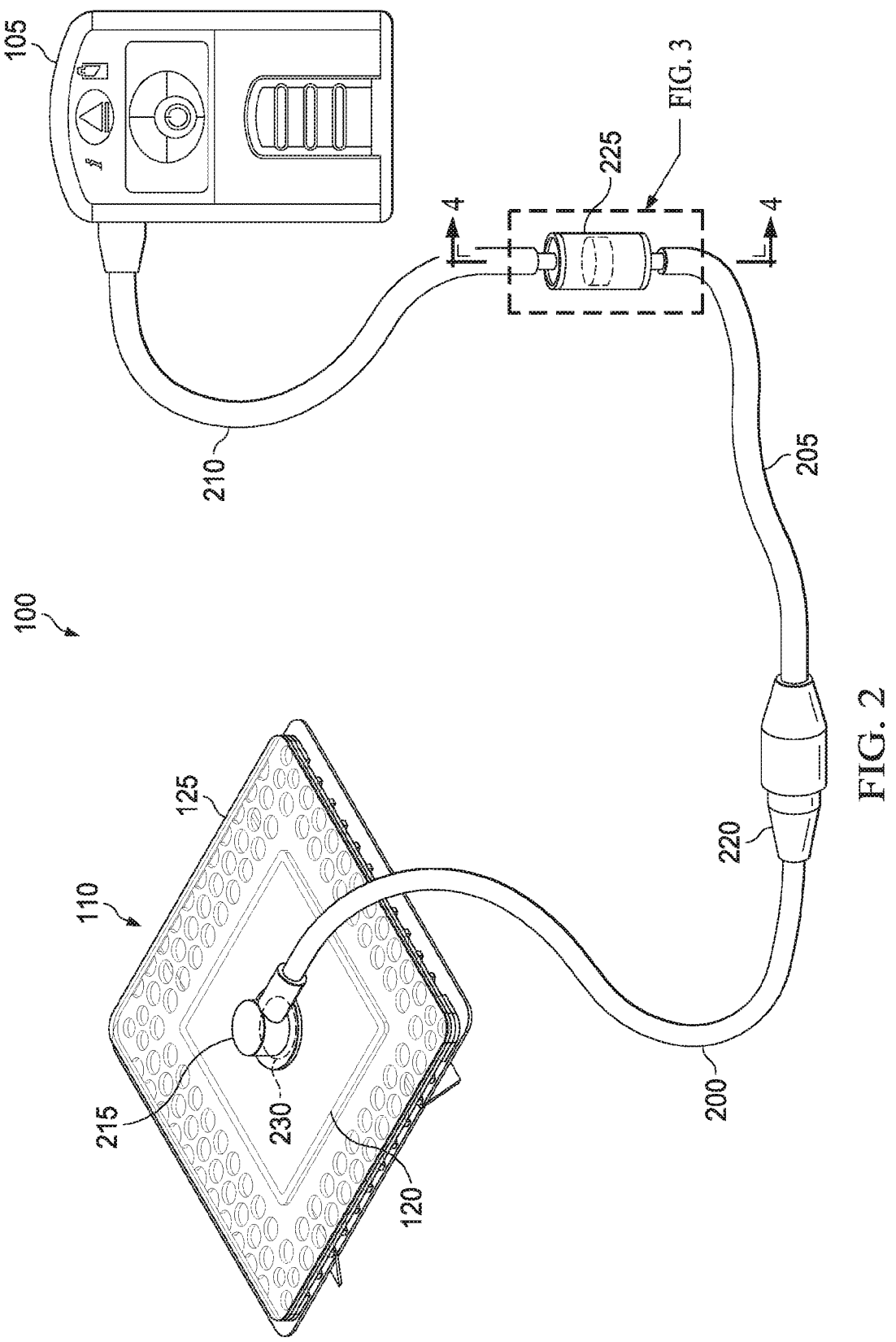
FIG. 2 is an isometric view of an example embodiment of the therapy system of FIG. 1.
FIG. 3 is a detail exploded view of the example pneumatic accumulator of FIG. 2.
Figure 3:
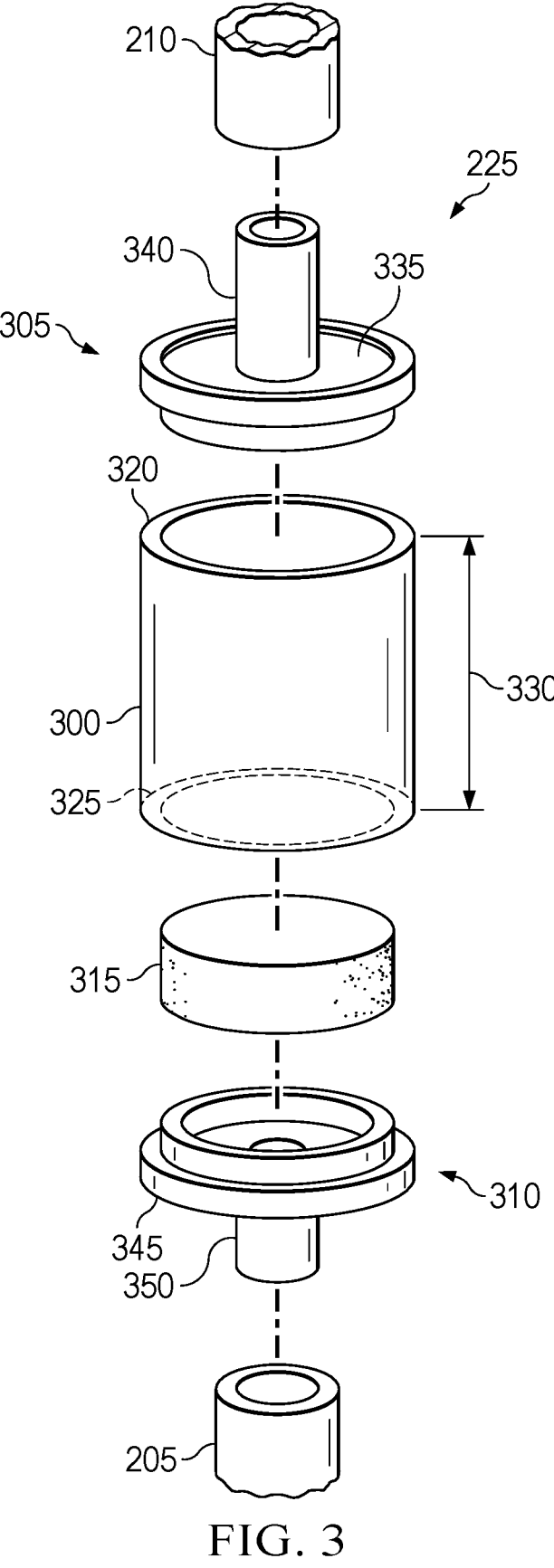

FIG. 2 is an isometric view of an example embodiment of the therapy system 100. In some embodiments, the dressing 110 may be fluidly coupled to the negative-pressure source 105 by one or more fluid conductors. As shown in FIG. 2, the therapy system 100 may include a first fluid conductor 200, a second fluid conductor 205, and a third fluid conductor 210. Each of the first fluid conductor 200, the second fluid conductor 205, and the third fluid conductor 210 may be a flexible tube. The therapy system 100 may also include a dressing interface 215, an inline connector 220, and a pneumatic accumulator 225 fluidly coupled to the negative-pressure source 105 and the dressing 110. In the example embodiment of FIG. 2, the therapy system 100 does not include a pouch 115 and fluids from a tissue site are stored in the dressing 110.

In some embodiments, the dressing interface 215 may be an elbow connector. A first end of the first fluid conductor 200 may be fluidly coupled with the dressing interface 215. The cover 125 may include an aperture 230, or the aperture 230 may be cut into the cover 125 before or after positioning the cover 125 over the tissue interface 120. The position of the aperture 230 may be off-center or adjacent to an end or edge of the cover 125. In other examples, the aperture 230 may be centrally disposed. The dressing interface 215 can be placed over the aperture 230 to provide a fluid path between the first fluid conductor 200 and the tissue interface 120. In other examples, the first fluid conductor 200 may be inserted directly through the cover 125 into the tissue interface 120.

A second end of the first fluid conductor 200 may be fluidly coupled to the inline connector 220. In some embodiments, the inline connector 220 may be a luer connector. A first end of the second fluid conductor 205 may be fluidly coupled to the inline connector 220 opposite the first fluid conductor 200. A second end of the second fluid conductor 205 may be fluidly coupled to the pneumatic accumulator 225. A first end of the third fluid conductor 210 may be fluidly coupled to the pneumatic accumulator 225 opposite the second fluid conductor 205. A second end of the third fluid conductor 210 may be fluidly coupled to the negative-pressure source 105. The dressing interface 215, the first fluid conductor 200, the inline connector 220, the second fluid conductor 205, the pneumatic accumulator 225, and the third fluid conductor 210 may provide a fluid path between the dressing 110 and the negative-pressure source 105.

Although the inline connector 220 and the pneumatic accumulator 225 are shown as separate components, in some embodiments, the inline connector 220 and the pneumatic accumulator 225 may be integrally formed. Although the dressing interface 215 and the pneumatic accumulator 225 are shown as separate components, in some embodiments, the dressing interface 215 and the pneumatic accumulator 225 may be integrally formed. Although the negative-pressure source 105 and the pneumatic accumulator 225 are shown as separate components, in some embodiments, the negative-pressure source 105 and the pneumatic accumulator 225 may be integrally formed.

FIG. 3 is a detail exploded view of the pneumatic accumulator 225 of FIG. 2. In some embodiments, the pneumatic accumulator 225 may include or be formed of a housing 300, a first end cap 305, and a second end cap 310. In some embodiments, the pneumatic accumulator 225 may also include a filter 315.

In some embodiments, the housing 300 may be formed of a rigid wall. The rigid wall may have a variety of shapes, including but not limited to, cylindrically-shaped and oval-shaped. A housing 300 having a cylindrical or substantially round shape without hard corners may not reduce patient comfort if a patient sits or lays on the housing 300. As shown in the example of FIG. 3, the housing 300 may be formed of a tubular member. The housing 300 may include a first end 320 and a second end 325. The first end 320 and the second end 325 may be open. In some embodiments, the housing 300 may have a length 330 in a range from about 10 millimeters to about 50 millimeters. In some embodiments, the housing 300 may have a length 330 of about 25 millimeters. The first end cap 305 may be configured to be coupled to the first end 320 of the housing 300 and the second end cap 310 may be configured to be coupled to the second end 325 of the housing 300.

The first end cap 305 may include a first wall 335 and a first port 340. In some embodiments, at least a portion of the first wall 335 may be elastomeric. The second end cap 310 may include a second wall 345 and a second port 350. In some embodiments, at least a portion of the second wall 345 may be elastomeric. The first wall 335 and the second wall 345 may include or be formed of a variety of materials, including but not limited to, thermoplastic elastomer (TPE), thermoplastic vulcanizates (e.g., Santoprene™ available from ExxonMobil), and/or polyvinylchloride (PVC). In some embodiments, the first port 340 and the second port 350 may include or be formed of the same material as the first wall 335 and the second wall 345, respectively. In some embodiments, the first port 340 and the second port 350 may include or be formed of acrylonitrile butadiene styrene (ABS) and/or a polycarbonate/acrylonitrile butadiene styrene (PC/ABS) blend. In some embodiments, the first port 340 may be co-injection molded with the first wall 335, and the second port 350 may be co-injection molded with the second wall 345. In some embodiments, the first port 340 and the second port 350 may be more rigid than the first wall 335 and the second wall 345, respectively. An end of the third fluid conductor 210 may couple to the first port 340 and an end of the second fluid conductor 205 may couple to the second port 350.

Figure 4:
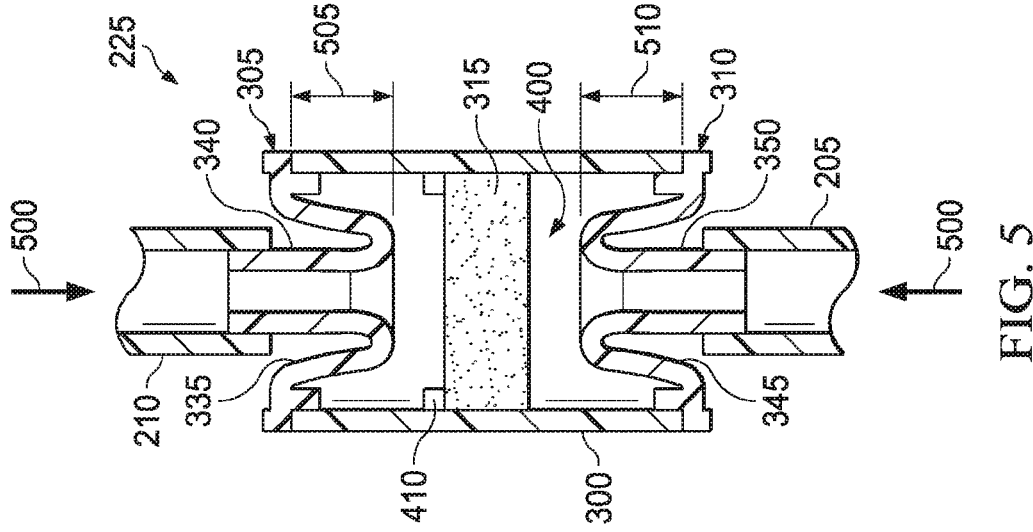
FIG. 4 is a cross-sectional view of the pneumatic accumulator of FIG. 2 taken along line 4-4.

FIG. 4 is a cross-sectional view of the pneumatic accumulator 225 of FIG. 2 taken along line 4-4. The first end cap 305 and the second end cap 310 may be coupled to the first end 320 and the second end 325, respectively, of the housing 300. For example, the first wall 335 may be sealed to the first end 320 and the second wall 345 may be sealed to the second end 325 by a weld or an adhesive. The first end cap 305, the second end cap 310, and the housing 300 may cooperate to form a chamber 400. The chamber 400 may be sealed by the housing 300, the first wall 335, and the second wall 345. The second port 350 may form an inlet into the chamber 400 and the first port 340 may form an outlet from the chamber 400. The second port 350 and the first port 340 may provide a flow path through the chamber 400 of the housing 300. The chamber 400 may have a first volume when the pressure inside the chamber 400 is at ambient pressure. In some embodiments, the first volume of the chamber 400 may range from about 2 cubic centimeters (cc) to about 5 cubic centimeters (cc). In some embodiments, the first volume of the chamber 400 may be about 3 cubic centimeters (cc).

The filter 315 may be disposed inside the chamber 400. In some embodiments, the filter 315 may be a gel-blocking filter, which may be configured to become gel-blocked (e.g. to prevent passage of liquid) upon contact and/or saturation with liquid. For example, the filter 315 may be configured to gel-block if liquid is drawn from the dressing 110 into one or more of the first fluid conductor 200 and the second fluid conductor 205. In some embodiments, the filter 315 may comprise a sintered polymer, which may swell on contact with water. Suitable polymers may include, for example, fluoropolymers such as polytetrafluoroethylene (PTFE), polyvinylidene fluoride (PVdF), or fluorinated ethylenepropylene (FEP); chlorofluoropolymers, such as polychlorotrifluoroethylene (PCTFE); polyolefins such as high density polyethylene (HDPE), polypropylene (PP), cyclic olefin copolymer (COC), or polymethylpentene (PMP); polyvinyl acetate (PVAc) or ethylene vinyl acetate (EVA); polycarbonate (PC); polyesters such as polyethylene terephthalate (PET) or PET copolymers (PETG); or polysulphones or polyethersulphones. Additionally, the filter 315 may be coated to enhance hydrophobicity in some embodiments. In some embodiments, the suitable polymers may be formed into membranes or sintered (particularly for PVAc, EVA, polyolefins, and fluoropolymers). In some embodiments, the filter 315 may comprise sintered polymers manufactured by Porex Filtration Group. In some embodiments, the filter 315 may be sized and shaped to press fit within the chamber 400. For example, if the housing 300 is cylindrical in shape and has a certain inner diameter, the filter 315 may also be cylindrical in shape have a diameter slightly larger than the inner diameter of the housing 300. In some embodiments, the filter 315 may have length 405 of about 5 millimeters. In some embodiments, a stop, such as an annular ring 410 may be located inside the housing 300. The annular ring 410 may aid in assembly of the pneumatic accumulator 225 and may ensure proper placement of the filter 315 in the chamber 400. As shown in FIG. 4, the filter 315 may be located centrally in the housing 300 such that it may be equidistant from the first end cap 305 and the second end cap 310. The annular ring 410 may be located in the chamber 400 between the filter 315 and the negative-pressure source 105. The annular ring 410 may prevent the filter 315 from being drawn toward the negative-pressure source 105 under the application of negative pressure. The annular ring 410 may thus prevent movement of the filter 315 in the housing 300.

In some embodiments, some or all of the housing 300 may be transparent so that the chamber 400 of the pneumatic accumulator 225 can be viewed. For example, the housing 300 may include a window 415. If liquid enters the chamber 400, the liquid can be viewed through the window 415. Liquid in the chamber 400 may indicate that the dressing 110 is full. In some embodiments, the filter 315 may release a dye if liquid comes into contact with the filter 315. The dye may be viewed through the window 415.

As further shown in FIG. 4, the first port 340 may be coupled with the third fluid conductor 210 and the second port 350 may be coupled with the second fluid conductor 205. For example, the first port 340 and the second port 350 may be inserted into the third fluid conductor 210 and the second fluid conductor 205, respectively. The first port 340 may be fluidly coupled with negative-pressure source 105, for example, by the third fluid conductor 210. The second port 350 may be fluidly coupled with the dressing 110, for example, by the second fluid conductor 205. The chamber 400 may be fluidly coupled with the negative-pressure source 105 and the dressing 110. Accordingly, negative pressure may be supplied to the chamber 400 by the negative-pressure source 105, and negative pressure may be supplied to the dressing 110 through the chamber 400 by the negative-pressure source 105.

Figure 5:
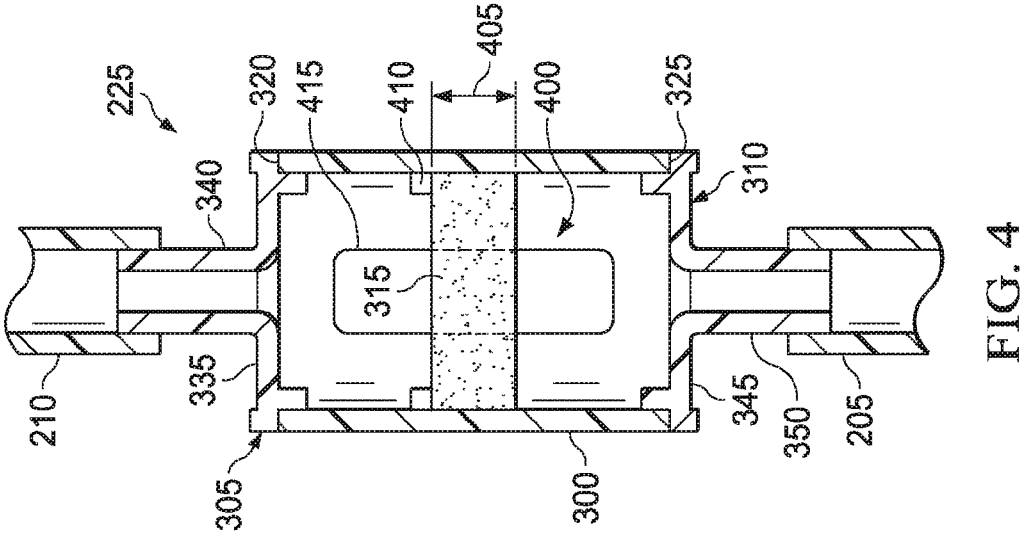
FIG. 5 is a cross-sectional view of the pneumatic accumulator of FIG. 4 under the application of negative pressure.

FIG. 5 is a cross-sectional view of the pneumatic accumulator 225 of FIG. 4 under the application of negative pressure. In some embodiments, in response to the application of negative pressure to the chamber 400, one or both of the first wall 335 and the second wall 345 may deflect inward, toward one another as shown by arrows 500. The deflection of the first wall 335 and/or the second wall 345 may reduce the volume of the chamber 400 from the first volume to a second volume. The chamber 400 may have a variable volume.

In some embodiments, the first wall 335 may be configured to deflect inward a maximum deflection distance 505 in a range of about 5 millimeters to about 15 millimeters if the chamber is subjected to negative pressure of about 125 mmHg. For example, in some embodiments, the first wall 335 may have a hardness of 50 Shore and may be configured to deflect inward a maximum deflection distance 505 in a range of about 8 millimeters to about 10 millimeters if the chamber is subjected to negative pressure of about 125 mmHg. In some embodiments, the second wall 345 may be configured to deflect inward a maximum deflection distance 510 in a range of about 5 millimeters to about 15 millimeters if the chamber is subjected to negative pressure of about 125 mmHg. For example, in some embodiments, the second wall 345 may have a hardness of 50 Shore and may be configured to deflect inward a maximum deflection distance 510 in a range of about 8 millimeters to about 10 millimeters if the chamber is subjected to negative pressure of about 125 mmHg. In some embodiments, the maximum deflection distance 505 of the first wall 335 and the maximum deflection distance 510 of the second wall 345 may be reached when the negative pressure in the chamber 400 reaches 125 mmHg. In some embodiments, the maximum deflection distance 505 of the first wall 335 and the maximum deflection distance 510 of the second wall 345 may be equal. In some embodiments, the maximum deflection distance 505 of the first wall 335 and the maximum deflection distance 510 of the second wall 345 may be unequal. For example, the maximum deflection distance 505 of the first wall 335 may be less than the maximum deflection distance 510 of the second wall 345, or the maximum deflection distance 505 of the first wall 335 may be greater than the maximum deflection distance 510 of the second wall 345.

The maximum deflection distance 505 and maximum deflection distance 510 may be tuned by altering the stiffness of the first wall 335 and the second wall 345, respectively. The maximum deflection distance 505 and maximum deflection distance 510 may be modified based on the length 330 of the housing 300 and the Shore hardness of the first wall 335 and the second wall 345, respectively. In some embodiments, the length 330 of the housing 300, the maximum deflection distance 505, the maximum deflection distance 510, and the length 405 of the filter 315 may be selected such that the first wall 335 and the second wall 345 do not contact the filter 315 under negative pressure. For example, testing has shown that a first wall 335 and a second wall 345 with a 50 Shore hardness may each deform by about 8 millimeters to about 10 millimeters, thus the length 330 of the housing 300 of about 25 millimeters is sufficient to prevent the first wall 335 and the second wall 345 from contacting the filter 315 having a length 405 of about 5 millimeters.

Figure 6:
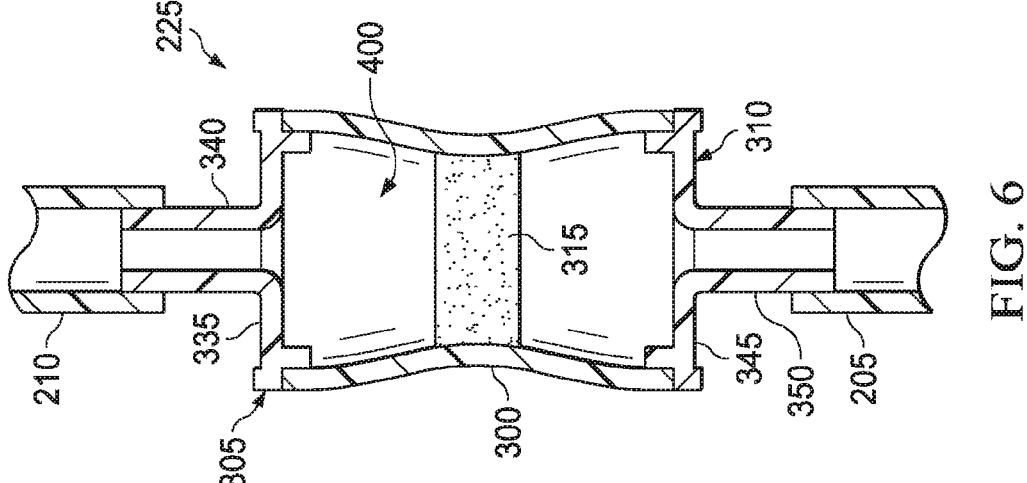
FIG. 6 is a cross-sectional view of another example embodiment of the pneumatic accumulator that can be associated with some embodiments of the therapy system.

FIG. 6 is a cross-sectional view of another example embodiment of the pneumatic accumulator 225 that can be associated with some embodiments of the therapy system 100. The pneumatic accumulator 225 in FIG. 6 is shown under the application of negative pressure. In the example embodiment of FIG. 6, the housing 300 may be elastomeric, whereas the first wall 335 and the second wall 345 may be rigid. For example, the housing 300 may be an elastomeric cylindrical sidewall that may radially collapse under the application of negative pressure. As shown in FIG. 6, the elastomeric cylindrical sidewall of the housing 300 deflects inward. The housing 300 may be a deformable portion of the pneumatic accumulator 225.

Figure 7:
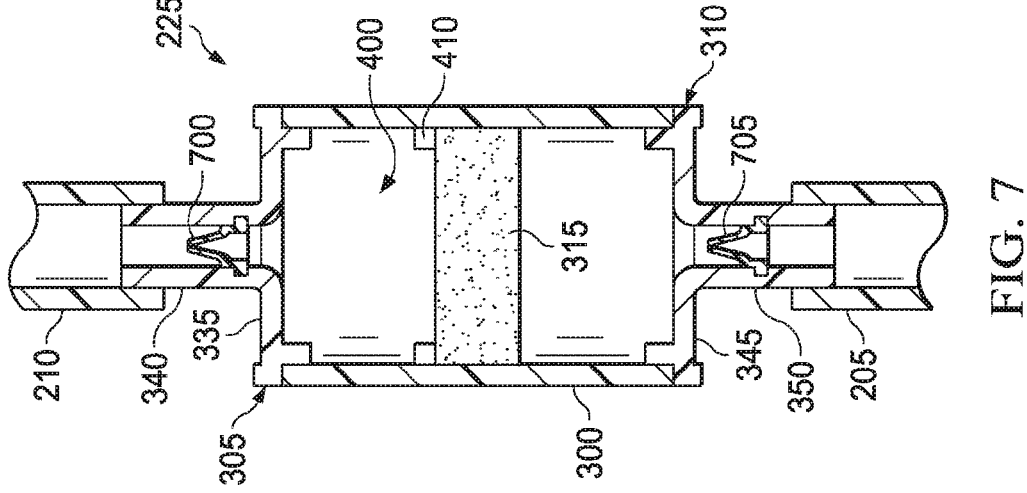
FIG. 7 is a cross-sectional view of another example embodiment of the pneumatic accumulator that can be associated with some embodiments of the therapy system.

FIG. 7 is a cross-sectional view of another example embodiment of the pneumatic accumulator 225 that can be associated with some embodiments of the therapy system 100. In some embodiments, the first end cap 305 may further include a first valve 700 in fluid communication with the first port 340. For example, the first valve 700 may be a one-way valve, such as a duckbill valve. In some embodiments, the first valve 700 may be disposed in the first port 340. Additionally, or alternatively, in some embodiments, the second end cap 310 may further include a second valve 705 in fluid communication with the second port 350. For example, the second valve 705 may be a one-way valve, such as a duckbill valve. In some embodiments, the second valve 705 may be disposed in the second port 350. The first valve 700 and the second valve 705 may be configured to allow negative pressure to flow toward the dressing 110 but prevent the flow of negative pressure back toward the negative-pressure source 105.

Negative pressure may be supplied to the pneumatic accumulator 225 through the third fluid conductor 210 by the negative-pressure source 105. If the cracking pressure of the first valve 700 is reached, the first valve 700 is configured to open, allowing negative pressure to be supplied to the chamber 400. Additionally, if the cracking pressure of second valve 705 is reached, the second valve 705 is configured to open, allowing negative pressure to be supplied to the dressing 110. If a leak occurs upstream of the pneumatic accumulator 225, for example at the interface between the dressing 110 and the tissue site, positive pressure may enter the therapy system 100 and may flow to the second valve 705. If the cracking pressure of the second valve 705 is reached, then the second valve 705 may open and the negative pressure stored in the chamber 400 of the pneumatic accumulator 225 may be supplied to the dressing 110. In some embodiments, the cracking pressure of the first valve 700 and the second valve 705 may be equal. In some embodiments, the cracking pressure of the first valve 700 may be less than the cracking pressure of the second valve 705. In some embodiments, the cracking pressure of the first valve 700 may be greater than the cracking pressure of the second valve 705. The cracking pressures of the first valve 700 and the second valve 705 may be designed to tune the negative pressure delivery to and from the chamber 400.

Figures 8, 9:
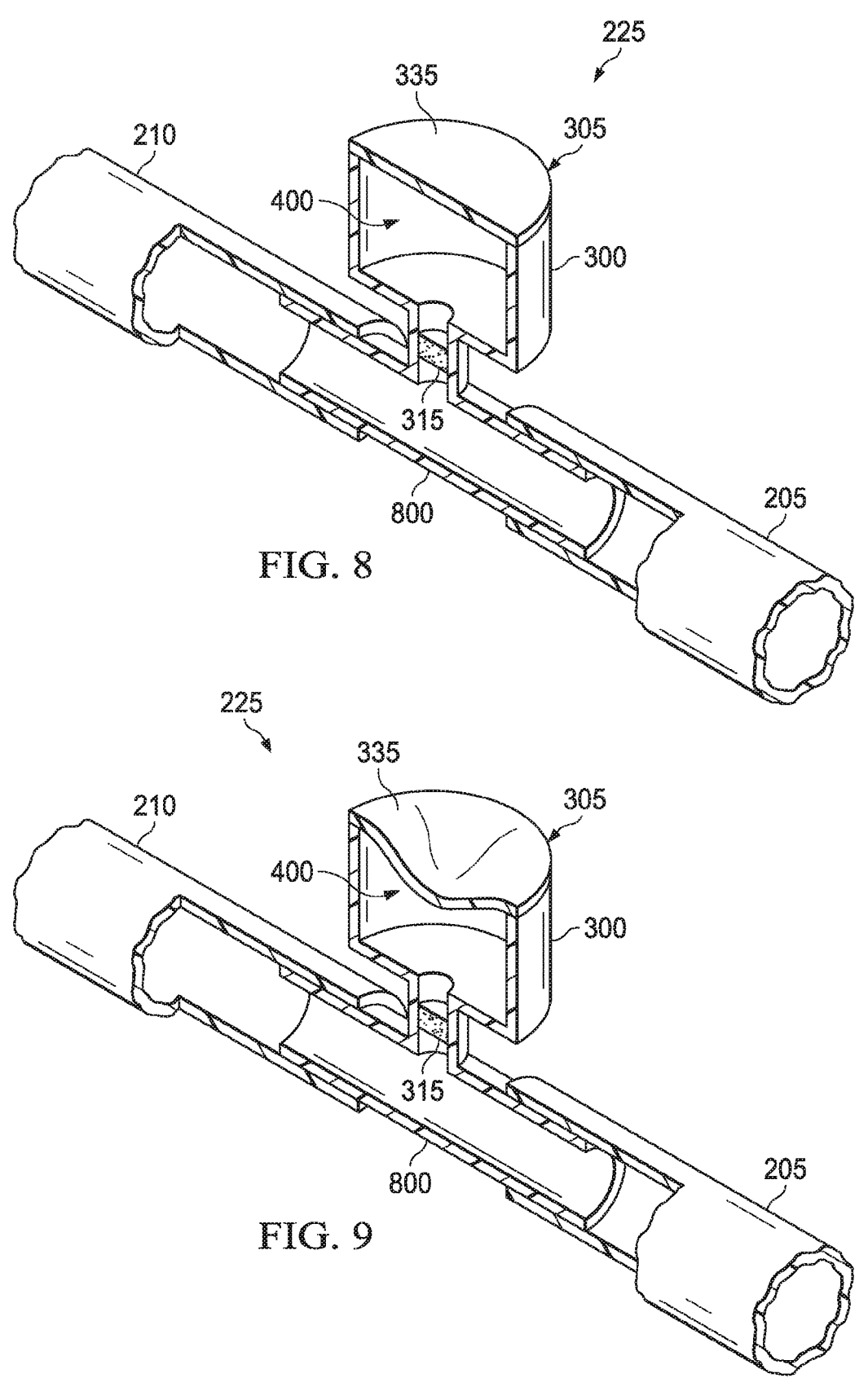
FIG. 8 is a partial cut-away isometric view of another example embodiment of the pneumatic accumulator that can be associated with some embodiments of the therapy system.
FIG. 9 is a partial cut-away isometric view of the pneumatic accumulator of FIG. 8 under the application of negative pressure.

FIG. 8 is a partial cut-away isometric view of another example embodiment of the pneumatic accumulator 225 that can be associated with some embodiments of the therapy system 100. In some embodiments, the pneumatic accumulator 225 may include the housing 300 and the first end cap 305. As shown in FIG. 8, the first end cap 305 may include only the first wall 335, wherein at least a portion of the first wall 335 is elastomeric. The pneumatic accumulator 225 may further include a port 800 that fluidly couples the chamber 400 to the dressing 110 and the negative-pressure source 105. For example, the port 800 may be a tee connection between the second fluid conductor 205 and the third fluid conductor 210. In some embodiments, the port 800 may be integrally formed with the housing 300. In some embodiments, the filter 315 may be disposed within the port 800. In the example embodiment of FIG. 8, the housing 300 may be rigid and the first wall 335 may be a deformable portion of the pneumatic accumulator 225.

FIG. 9 is a partial cut-away isometric view of the pneumatic accumulator 225 of FIG. 8 under the application of negative pressure. In some embodiments, in response to the application of negative pressure to the chamber 400, the first wall 335 may deflect into the chamber 400 toward the port 800. The deflection of the first wall 335 may reduce the volume of the chamber 400 from the first volume to a second volume, wherein the second volume may be about 50% or less than the first volume.

Figures 10, 11:
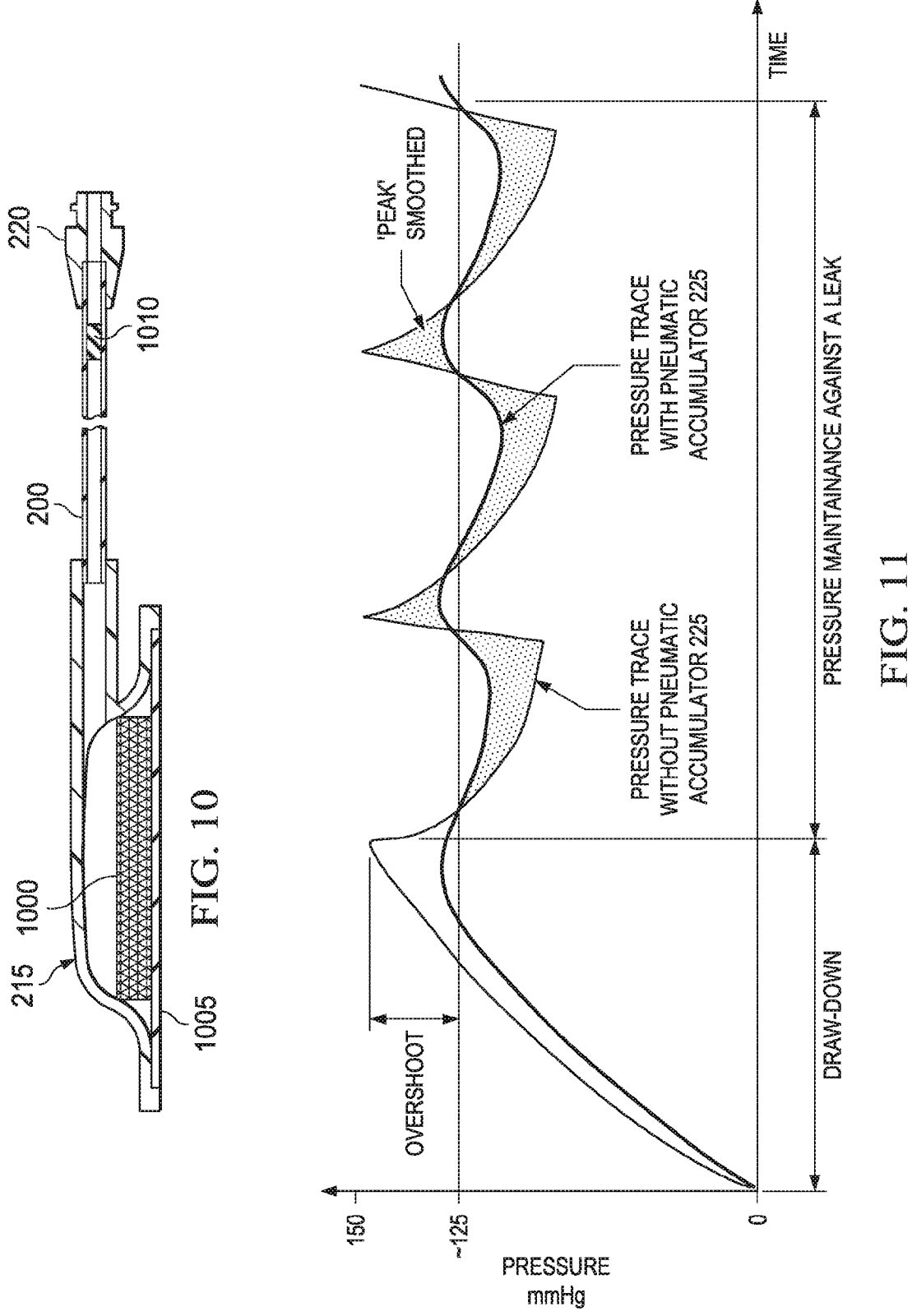
FIG. 10 is a cross-sectional view of an example embodiment of a dressing interface, a first fluid conductor, and a portion of an inline connector of FIG. 2.
FIG. 11 is a chart illustrating operation of an embodiment of the therapy system with a pneumatic accumulator and a therapy system without a pneumatic accumulator.

FIG. 10 is a cross-sectional view of an example embodiment of the dressing interface 215, the first fluid conductor 200, and a portion of the inline connector 220 of FIG. 2. In some embodiments, the dressing interface 215 may carry an odor filter 1000 configured to substantially preclude the passage of odors from the tissue site. Further, in some embodiments, the dressing interface 215 may carry a primary hydrophobic filter 1005 configured to substantially preclude the passage of liquids out of the dressing 110. The odor filter 1000 and the primary hydrophobic filter 1005 may be disposed in the dressing interface 215 or other suitable location such that fluid communication between the negative-pressure source 105 and the dressing 110 is provided through the odor filter 1000 and the primary hydrophobic filter 1005.

The odor filter 1000 may be comprised of a carbon material in the form of a layer or particulate. For example, the odor filter 1000 may comprise a woven carbon cloth filter such as those manufactured by Chemviron Carbon, Ltd. of Lancashire, United Kingdom (www.chemvironcarbon.com). The primary hydrophobic filter 1005 may be comprised of a material that is liquid impermeable and vapor permeable. For example, the primary hydrophobic filter 1005 may comprise a material manufactured under the designation MMT-314 by W.L. Gore & Associates, Inc. of Newark, Delaware, United States, or similar materials. The primary hydrophobic filter 1005 may be provided in the form of a membrane or layer.

In some embodiments, a secondary hydrophobic filter 1010 may be disposed in the first fluid conductor 200 such that fluid communication between the negative-pressure source 105 and the dressing 110 is provided through the secondary hydrophobic filter 1010. In some embodiments, the secondary hydrophobic filter 1010 may be a gel-blocking filter, which may be configured to become gel-blocked (e.g. to prevent passage of liquid) upon contact and/or saturation with liquid. For example, the secondary hydrophobic filter 1010 may be configured to gel-block if liquid is drawn from the dressing 110 into the first fluid conductor 200. In some embodiments, the secondary hydrophobic filter 1010 may comprise a sintered polymer, which may swell on contact with water. Suitable polymers may include, for example, fluoropolymers such as polytetrafluoroethylene (PTFE), polyvinylidene fluoride (PVdF), or fluorinated ethylenepropylene (FEP); chlorofluoropolymers, such as polychlorotrifluoroethylene (PCTFE); polyolefins such as high density polyethylene (HDPE), polypropylene (PP), cyclic olefin copolymer (COC), or polymethylpentene (PMP); polyvinyl acetate (PVAc) or ethylene vinyl acetate (EVA); polycarbonate (PC); polyesters such as polyethylene terephthalate (PET) or PET copolymers (PETG); or polysulphones or polyethersulphones. Additionally, the secondary hydrophobic filter 1010 may be coated to enhance hydrophobicity in some embodiments. In some embodiments, the suitable polymers may be formed into membranes or sintered (particularly for PVAc, EVA, polyolefins, and fluoropolymers). In some embodiments, the secondary hydrophobic filter 1010 may comprise sintered polymers manufactured by Porex Filtration Group.

In operation, negative pressure may be supplied by the negative-pressure source 105 to the dressing 110 through the pneumatic accumulator 225. One or more of the first wall 335 and the second wall 345 may be drawn inward into the chamber 400 of the pneumatic accumulator 225 as negative pressure is applied to the chamber 400. The pneumatic accumulator 225 may store negative pressure. Additionally, potential energy may be stored in the deformed first wall 335 and/or the deformed second wall 345. If the negative-pressure source 105 is turned off and/or the negative pressure at the dressing 110 drops, negative pressure stored in the chamber 400 of the pneumatic accumulator 225 may be supplied to the dressing 110. Additionally, one or more of the deformed first wall 335 and the deformed second wall 345 may partially or completely return to their un-deformed state, generating additional negative pressure that can be supplied to the dressing 110. The pneumatic accumulator 225 can store negative pressure spikes from the negative-pressure source 105 and then may release this stored negative pressure at a later time to the therapy system 100 if the therapy system 100 loses negative pressure.

FIG. 11 is a chart illustrating operation of an embodiment of the therapy system 100 with the pneumatic accumulator 225 and a therapy system without the pneumatic accumulator 225. Various therapy systems that have absorbent dressings but do not include an exudate container may have a low plenum volume. That is, they may have a low level of static air volume in the absorbent dressing due to the nature of the pressure, air, and fluid manifolding structures of the absorbent dressing and the tendency of the absorbent dressing to compress at negative pressure. In order to accommodate a high degree of leak in the system that may result from user application, negative-pressure sources having moderately large pumps are often used. These negative-pressure sources may be configured to be electrically efficient at a negative pressure of 125 mmHg with a system leak of about 40 cc/minute, thus reducing battery change frequency or the size of the power system. Such negative-pressure sources may reach this efficiency point by having high torque motors and large area pump heads or diaphragms with large displacement volumes. As the negative-pressure source operates, a large movement of the diaphragm and a large volume of air is moved, which works well if the leak is about 40 cc/minute. However, the objective of the therapy systems is to reduce or eliminate the leak, such that the desired negative pressure is reached at the dressing and the negative-pressure source is seldom activated. In situations where there is a low level leak in the therapy system, the negative-pressure source will activate periodically to maintain the desired negative pressure. However, as shown in FIG. 11, due to the large displacement volume of some negative-pressure sources, the negative-pressure source may cause an overshoot of the target pressure and additional significant pressure excursions, peaks, or spikes as the negative-pressure source attempts to maintain negative pressure against a leak. In such systems, there may be insufficient plenum volume in therapy systems with absorbent dressings to smooth out the pressure peaks or spikes caused by the negative-pressure source. For example, if the therapy system has a leak of about 10 cc/minute, the negative-pressure source may cause significant pressure excursions, which may be difficult for the controller to control and may result in aliasing of the sensor monitoring the negative pressure.

However, the systems, apparatuses, and methods described herein may provide significant advantages. For example, as also shown in FIG. 11, the pneumatic accumulator 225 overcomes the issues of low plenum volume therapy systems by providing a small, variable volume chamber 400 that smooths out any pressure peaks or spikes created by the negative-pressure source 105. The pneumatic accumulator 225 may reduce or prevent aliasing and/or pressure overshoots, as well as assisting with optimizing energy efficient hysteresis pressure control of the negative pressure applied to the tissue site. The pneumatic accumulator 225 may provide pressure smoothing capacity to the therapy system 100, which can reduce or eliminate pressure peaks caused by actuation of the negative-pressure source 105 which could otherwise be outside the control range of the therapy system 100. The pneumatic accumulator 225 can reduce or eliminate controller-experienced pump/volume-induced aliasing. Additionally, the pneumatic accumulator 225 provides additional vacuum storage capacity within the therapy system 100, which allows the negative-pressure source 105 to activate less often, resulting in increased efficiency. Moreover, the chamber 400 and the deformable members, such as the first wall 335 and the second wall 345, may increase the pressure smoothing effect beyond what can be achieved by having a small static (non-variable) volume. The pneumatic accumulator 225 may also act as an energy store within the therapy system 100 and may increase overall energy efficiency. Additionally, the filter 315 may also serve to prevent contamination of the negative-pressure source 105.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the pneumatic accumulator 225, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for reducing pressure spikes at a dressing of a negative-pressure therapy system, the apparatus comprising:
 a rigid tubular member having a first open end and a second open end;
 a first end cap coupled to the first open end, the first end cap comprising:
  a first wall, at least a portion of which is elastomeric; and
  a first port; and
 a second end cap coupled to the second open end; the second end cap comprising:
  a second wall, at least a portion of which is elastomeric; and
  a second port;
 wherein the rigid tubular member, the first end cap, and the second end cap cooperate to form a chamber having a first volume when the chamber is at ambient pressure;
 wherein the first port is configured to be fluidly coupled to a negative-pressure port and the second port is configured to be fluidly coupled to the dressing;
 wherein in response to an application of a negative pressure to the chamber, one or more of the first wall and the second wall are configured to deflect toward one another to reduce the volume of the chamber from the first volume to a second volume; and
 wherein the first wall is configured to deflect toward the second wall a first maximum deflection distance and the second wall is configured to deflect toward the first wall a second maximum deflection distance, and wherein a gap exists between the first wall and the second wall when the first wall is at the first maximum deflection distance and the second wall is at the second maximum deflection distance, such that a fluid is still permitted to flow through the apparatus when the first wall is at the first maximum deflection distance and the second wall is at the second maximum deflection distance.

2. The apparatus of claim 1, wherein the first volume is in a range of about 2 to about 5 cubic centimeters.

3. The apparatus of claim 1, further comprising a filter disposed within the chamber.

4. The apparatus of claim 3, wherein the filter is configured to gel in response to liquid contacting the filter.

5. The apparatus of claim 1, wherein one or more of the first wall and the second wall comprises thermoplastic elastomer (TPE), thermoplastic vulcanizates, polyurethane (PU), or polyvinyl chloride (PVC).

6. The apparatus of claim 1, wherein one or more of the first wall and the second wall are configured to deflect inward in a range of about 8 to about 10 millimeters in response to a negative pressure of 125 mmHg in the chamber.

7. The apparatus of claim 1, wherein one or more of the first port and the second port comprises ABS or PC/ABS.

8. The apparatus of claim 1, further comprising a first valve fluidly coupled to the first port and a second valve fluidly coupled to the second port.

9. The apparatus of claim 8, wherein the first valve is a one-way valve and the second valve is a one-way valve.

10. A system for treating a tissue site with negative pressure, the system comprising:

a dressing;

a negative-pressure source configured to be fluidly coupled to the dressing; and a pneumatic accumulator configured to be between the dressing and the negative-pressure source, the pneumatic accumulator comprising:

a housing comprising a rigid sidewall having a first open end and a second open end;

a first end cap coupled to the first open end, the first end cap having a first port and a first elastomeric member, the first port fluidly coupled to the negative-pressure source; and a second end cap coupled to the second open end, the second end cap having a second port and a second elastomeric member, the second port fluidly coupled to the dressing;

wherein the housing, the first end cap, and the second end cap define a chamber configured to be fluidly coupled to the dressing and the negative-pressure source, the chamber having a volume in a range of about 2 to about 5 cubic centimeters;

wherein under an application of negative pressure, the first elastomeric member and the second elastomeric member are configured to deform toward one another to reduce the volume of the chamber; and wherein the first elastomeric member is configured to deflect toward the second elastomeric member a first maximum deflection distance and the second elastomeric member is configured to deflect toward the first elastomeric member a second maximum deflection distance, and wherein a gap exists between the first elastomeric member and the second elastomeric member when the first elastomeric member is at the first maximum deflection distance and the second elastomeric member is at the second maximum deflection distance, such that a fluid is still permitted to flow through the pneumatic accumulator when the first elastomeric member is at the first maximum deflection distance and the second elastomeric member is at the second maximum deflection distance.

11. The system of claim 10, wherein at least a portion of the pneumatic accumulator is transparent.

12. The system of claim 10, wherein the pneumatic accumulator is configured to reduce pressure spikes at the dressing.

13. The system of claim 10, further comprising a first valve fluidly coupled to the chamber and a second valve fluidly coupled to the chamber.

14. The system of claim 13, wherein the first valve is configured to open at a first cracking pressure to allow negative pressure to be applied to the chamber, and wherein the second valve is configured to open at a second cracking pressure to allow negative pressure to be applied to the dressing.

* * * * *